United States Patent [19]

Eckenhoff

[11] 4,350,271
[45] Sep. 21, 1982

[54] WATER ABSORBING FLUID DISPENSER

[75] Inventor: James B. Eckenhoff, Los Altos, Calif.

[73] Assignee: Alza Corporation, Palo Alto, Calif.

[21] Appl. No.: 180,353

[22] Filed: Aug. 22, 1980

[51] Int. Cl.³ .................................................. A61M 31/00
[52] U.S. Cl. .................................... 222/386.5; 128/260
[58] Field of Search ........................ 222/95, 92, 386.5; 128/260, 272

[56] References Cited

U.S. PATENT DOCUMENTS 3,865,108 2/1975 Hartop .............................. 222/95 X
4,203,439 5/1980 Theeuwes ........................ 222/386.5

Primary Examiner—Joseph J. Rolla
Attorney, Agent, or Firm—Steven F. Stone; Edward L. Mandell; Paul L. Sabatine

[57] ABSTRACT

A fluid dispenser that operates by absorbing water is disclosed. The dispenser includes a rigid water permeable housing; a water insoluble, water swellable composition that fills a segment of the space within the housing, a lipophilic fluid charge that fills the remainder of the space within the housing and that is immiscible in the water-swellable composition, and an outlet through the housing that communicates with the fluid charge. In operation the water swellable composition absorbs water, expands, and in piston-like fashion displaces the fluid charge from the dispenser via the outlet.

7 Claims, 2 Drawing Figures

WATER ABSORBING FLUID DISPENSER

DESCRIPTION

1. Technical Field

This invention relates to an active agent dispenser that absorbs water and swells to displace a lipophilic fluid charge from the dispenser in a rate-controlled fashion.

2. Background Art

U.S. Pat. No. 3,865,108 describes a medicine dispenser that operates by absorbing water. The components of this dispenser are arranged concentrically and consist of: an inner collapsible tube that contains the medicine; a water swellable base member that surrounds all but one end of the tube; and a water permeable outer skin around the base member. The outer skin is said to be an optional element—used to keep the base element intact. When placed in a water containing environment, the base member absorbs water from the environment and expands. Such expansion squeezes the collapsible tube causing the medicine to be expelled from the free end of the tube.

The present invention is functionally similar to the dispenser of U.S. Pat. No. 3,865,108 in that it, too, involves a water swellable composition that absorbs water, and expands to displace the composition to be dispensed. In structure, however, the present invention is much different from the patent dispenser. The more significant differences are: (1) the composition that is dispensed is not confined in a collapsible tube, (2) the components are not arranged concentrically, and (3) the water swellable composition and fluid that is dispensed are in direct contact.

DISCLOSURE OF INVENTION

The invention is a fluid dispenser for use in a water-containing environment comprising in combination:
(a) a rigid, water permeable housing;
(b) a water insoluble, water-swellable composition filling a portion of the space within the housing and being in contact with the housing;
(c) a lipophilic fluid composition filling the remainder of the space within the housing, said fluid composition being substantially immiscible in the water swellable composition; and
(d) fluid composition outlet means in the housing that communicates with the fluid composition.

DETAILED DESCRIPTION OF THE EMBODIMENTS OF THE DRAWINGS

Figure 1:
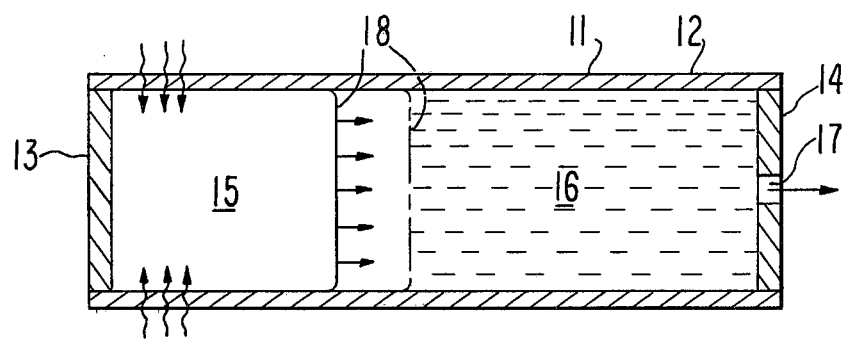
FIG. 1 is an enlarged cross-sectional partly schematic view of one embodiment of the invention.

FIG. 1 illustrates the preferred embodiment of the invention. The dispenser shown in FIG. 1 is generally designated 11. Dispenser 11 consists of the following elements: a tubular housing 12; a pair of plugs or caps 13, 14 in the ends of housing 12; a water insoluble, water swellable composition 15 that fills a segment of the space within housing 12; a fluid composition 16, such as an active agent composition in fluid form, that fills the remainder of the space within the housing; and an orifice 17 in plug 14. Housing 12 is cylindrical but it could just as well have another regular shape or be shaped irregularly. It is also shape-retaining, that is, it is sufficiently rigid to be substantially undeformed by the swelling of composition 15. Housing 12 is semipermeable, being permeable to water and substantially impermeable to compositions 15 and 16. Examples of polymers that may be used to make housing 12 are cellulose esters and ethers such as cellulose acetate and cellulose butyrate and the other semipermeable film-forming compositions disclosed in U.S. Pat. No. 3,760,984 at col 4, line 53 to col 5, line 39 and in U.S. Pat. No. 3,995,631 at col 7, line 40 to col 8, line 15, the disclosure of the latter of which is incorporated herein by reference. These compositions may contain minor amounts of additives such as fillers, stabilizers, pigments, water flux enhancers, and water flux attenuators.

Plugs 13 and 14 are made from materials that are impermeable to compositions 15 and 16, respectively, and that are capable of forming a fluid tight fit with housing 12 such as by adhesion, fusion, or press-fitting. Plugs 13 and 14 are also rigid and do not yield or deform upon application of pressure.

Composition 15 fills a segment of the space within housing 12 contiguous to plug 13 and a portion of the inner surface of housing 12. It is capable of absorbing water and swelling in response thereto to increase in volume. Preferably it is able to absorb sufficient water to cause it to expand to fill the entire space within housing 12. Examples of water insoluble, water swellable compositions that may be used in dispenser 11 are disclosed in U.S. Pat. No. 3,865,108 at column 2, lines 35 to 50 and in U.S. Pat. No. 4,207,893 at column 4, lines 23 to 47, the disclosure of the latter of which is incorporated herein by reference. Preferably, composition 15 consists essentially of polyethylene oxide having a molecular weight in the range of about 100,000 to about 4,000,000.

Composition 16 is the material that is expelled from dispenser 11. As shown in FIG. 1, it occupies the remaining space within housing 12 that is not occupied by composition 15. As such, it is in direct contact with composition 15 at interface 18. Composition 16 is sufficiently lipophilic to make it substantially immiscible in composition 15. By "substantially immiscible" it is meant that the two compositions remain as separate phases with a well-defined interface 18. Usually their solubility in each other will be less than about one mg/ml. Composition 16 is fluid, that is, it is capable of flowing and yields to pressure. Accordingly it will typically be in the form of a liquid, paste, gel, suspension, or other type of flowable semisolid. In most applications, composition 16 will be an active agent composition. Such compositions comprise a compound or mixture of compounds that can be dispensed to produce a predetermined, useful effect. Examples of active agents are pesticides, germicides, biocides, algicides, rodenticides, fungicides, insecticides, antioxidants, plant growth promoters, plant growth inhibitors, preserving agents, disinfectants, sterilization agents, catalysts, chemical reactants, fermentation agents, cosmetics, foods, nutrients, food supplements, drugs, vitamins, sex sterilants, fertility inhibitors, fertility promoters, air purifiers, microorganism attenuators, and other compositions that benefit the environment, surroundings, or habitat, including animals and humans.

Dispenser 11 operates as follows. It is activated by placing it in a water containing environment. For instance, in the case of embodiments that dispense drugs it is inserted into a body cavity or implanted within the body. Once in such an environment, water from the environment permeates through semipermeable housing 12 (represented by wavy arrows in FIG. 1) and is absorbed by composition 15 causing the composition to swell. Since the housing and end plugs of the dispenser are rigid, composition 15 can only expand unidirectionally toward plug 14. Such expansion is represented by the axially directed straight arrows at interface 18. Composition 15 in a partly expanded state is represented by interface 18 in phantom. As composition 15 expands axially, it exerts pressure on fluid composition 16 causing composition 16 to be expelled from the dispenser via orifice 17. It thus acts as a piston to displace composition 16. The rate at which composition 16 is expelled will depend upon the water permeability and dimensions of the semipermeable housing and the swelling characteristics of the water swellable composition. In the case of an active composition 16 of agent concentration $C_D$, the mass flow rate of agent from the dispenser is given by the equation:

$$(dm/dt) = A \cdot K_o \cdot C_D$$

where dm/dt is the mass flow rate, A is the cross-sectional area of interface 18, and $K_o$ is the swelling constant which in turn equals the water transmission rate of the housing divided by its thickness. Accordingly the dispensing rate may be varied by varying A, $K_o$ or $C_D$. The orifice 17 is sufficiently small to prevent convective or diffusive loss of composition 16 and sufficiently large to permit filling the dispenser and prevent hydrostatic pressure buildup during operation.

Figure 2:
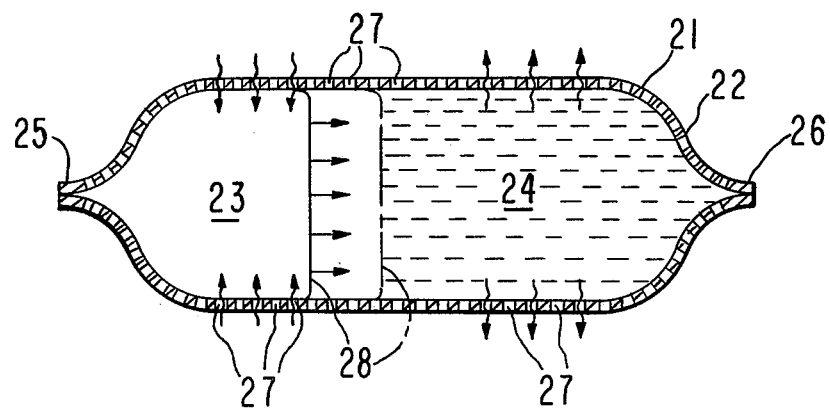
FIG. 2 is an enlarged cross-sectional partly schematic view of another embodiment of the invention.

FIG. 2 depicts another dispenser of the invention. The dispenser of FIG. 2 is generally designated 21. It differs from dispenser 11 as regards the structure and shape of the housing and the outlet means via which the fluid composition is expelled. Dispenser 21 consists of substantially rigid housing 22, a water insoluble, water swellable composition 23 and a lipophilic fluid composition 24. Housing 22 is made from a cylindrical tube of microporous polymer whose ends 25, 26 have been pinched and sealed by fusion, adhesion, or other suitable sealing means. Microporous housing 22 is permeable to water and to composition 24 but is impermeable to composition 23. In other words the micropores 26 in the wall of housing 22 are sized to permit passage of water and composition 24 but not composition 23. They will typically be on the order of 10 Angstroms to 100 micrometers in nominal diameter. Microporous materials are well known and examples of that may be used to make housing 22 are disclosed in U.S. Pat. No. 4,160,452 at column 15, line 11 to col 17, line 55, which disclosure is incorporated herein by reference.

When placed in an aqueous environment, water migrates through the micropores 27 in that portion of housing 22 contiguous to composition 23 (indicated by wavy arrows) and is absorbed by composition 23 causing it to swell and expand unidirectionally (indicated by axially directed arrows at the interface 28 between compositions 23, 24). As in the case of dispenser 11, there is substantially no mixing between compositions 23 and 24 and the expansion of composition 23 places a displacing pressure on composition 24. Composition 24 is not, however, expelled via a single orifice as is the case in dispenser 11. Instead it is expelled via the micropores 27 in the portion of housing 26 that is contiguous to composition 24. For a composition 24 of active agent concentration $C_D$, the mass flux of agent through the micropores is depicted by wavy arrows in FIG. 2 and is equal to $$J = (N\pi r^4 P/8\eta l) \cdot C_D$$

where J is the mass flux, N is the number of micropores with radius r, P is the displacing pressure exerted by composition 23, $\eta$ is the viscosity of composition 24, and l is the thickness the of microporous housing.

Modifications of the above described dispensers that are obvious to those of skill in the mechanical, chemical, and other related arts are intended to be within the scope of the following claims.

I claim:

1. Fluid dispenser for use in a water containing environment comprising:
   (a) a rigid, water permeable housing;
   (b) a water insoluble, water swellable composition filling a portion of the space within the housing and being in contact with the housing;
   (c) a fluid lipophilic composition filling the remainder of the space within the housing, said fluid composition being substantially immiscible in the water swellable composition; and
   (d) fluid composition outlet means in the housing that communicates with the fluid composition.

2. The dispenser of claim 1 wherein said lipophilic composition and said water swellable composition form therebetween a substantially contiguous interface extending substantially completely across said container.

3. The dispenser of claim 1 or 2 wherein the outlet means is a plurality of micropores in the housing that permit passage of the fluid composition when hydraulic pressure is applied to the fluid composition and do not permit passage of the water swellable composition.

4. The dispenser of claim 1 or 2 wherein the outlet means is a single orifice in the housing.

5. The dispenser of claim 1 or 2 wherein the water swellable composition is comprised of polyethylene oxide having a molecular weight in the range of about 100,000 to about 4,000,000.

6. The dispenser of claim 1 or 2 wherein said housing is tubular and provided with rigid ends resistant to the hydraulic pressure generated within said housing, said water swellable composition fills one end of said dispenser and said fluid lipophilic composition fills the other of said ends.

7. The dispenser of claim 6 wherein the outlet means is an orifice in said other end of said housing.

* * * * *